United States Patent [19]
Canal et al.

[11] Patent Number: 5,536,508
[45] Date of Patent: Jul. 16, 1996

[54] PHARMACEUTICAL COMPOSITIONS IN THE FORM OF PARTICLES SUITABLE FOR THE CONTROLLED RELEASE OF PHARMACOLOGICALLY ACTIVE SUBSTANCES AND PROCESS FOR PREPARING THE SAME COMPOSITIONS

[75] Inventors: Tiziana Canal; Mara Lucia Lovrecich; Fabio Carli, all of Trieste, Italy

[73] Assignee: Vectorpharma International S.p.A., Trieste, Italy

[21] Appl. No.: 139,051

[22] Filed: Oct. 21, 1993

Related U.S. Application Data

[63] Continuation of Ser. No. 794,905, Nov. 20, 1991, abandoned.

[30] Foreign Application Priority Data

Nov. 22, 1990 [IT] Italy .................. 22155REGA

[51] Int. Cl.⁶ .......................... A61K 9/50; A61K 47/30; A61K 47/32; A61F 2/02

[52] U.S. Cl. .................. 424/501; 424/423; 424/499; 424/501; 424/502; 514/772.3; 514/772.6; 514/774; 514/777

[58] Field of Search .................. 424/423, 484, 424/485, 486, 488, 489, 501, 502, 499, 501; 514/772.3, 772.6, 777, 774

[56] References Cited

U.S. PATENT DOCUMENTS

4,293,539 10/1981 Ludwig et al. .................. 424/489
4,962,091 10/1990 Eppstein et al. .................. 514/2

*Primary Examiner*—Carlos Azpuru
*Attorney, Agent, or Firm*—Birch, Stewart, Kolasch & Birch

[57] ABSTRACT

Pharmaceutical compositions in the form of particles comprising a biodegradable polymer and/or a polysaccharide jellifying and/or bioadhesive polymer, an amphiphilic polymer, an agent modifying the interface properties of the particles and a pharmacologically active substance. Said compositions exhibit improved biocompatibility features and allow a controlled release of the active substance.

34 Claims, No Drawings

PHARMACEUTICAL COMPOSITIONS IN THE FORM OF PARTICLES SUITABLE FOR THE CONTROLLED RELEASE OF PHARMACOLOGICALLY ACTIVE SUBSTANCES AND PROCESS FOR PREPARING THE SAME COMPOSITIONS

This application is a continuation of application Ser. No. 07/794,905 filed on Nov. 20, 1991, now abandoned.

DESCRIPTION

TECHNICAL FIELD OF THE INVENTION

The present invention relates to the preparation of novel pharmaceutical compositions in the form of particles consisting of composite materials which can be used for the controlled release of pharmacologically active substances.

BACKGROUND OF THE INVENTION

Pharmaceutical compositions in the form of particles are known, which comprise the active agent dissolved or dispersed in a polymer and which are suitable for the delayed release of some molecules of clinical interest after one single administration. Among the biodegradable polymers used for this purpose, the polylactic acid, polyglycolic acid and copolymer thereof proved to be effective in delaying the release of the drug. Also polymers of polysaccharide type have been used to modulate the release of drugs. Among those polymers xanthan, scleroglucan, ialuronic acid and chitosan proved to have good technological features and practically inexistent toxicity. Moreover some of these exhibit bioadhesive properties which render them specifically suitable to prolong the retaining time of pharmaceutical formulations in the administration sites. Both group of polymers is therefore widely used in manufacturing, for instance, microparticles comprising active agents whose release is modulated by them. Said particles systems may be prepared using techniques of emulsion whereby the active agent is dissolved or dispersed in a polymer solution and the resulting solution of dispersion is subsequently emulsified in a solvent in which the polymer is insoluble. The solvents are thereafter removed by evaporation (GB-A-2 077 692), by extraction with a second solvent (US-A-4 815 542) or by combination of the two techniques (BE-A-890 638). Moreover techniques may be found in the literature, which have been employed to modify the permeability and/of the biodegradation of the polymers which form the particle systems in such a way to exert an influence on the kinetic of the active agent release. For example there is described in the U.S. Pat. No. 4,479.911 the addition of an alkaline agent to the continuous phase used in preparing particle systems. Said agent increases the release rate of the active agent but the concentration range in which it may be used is limited by the higher degradation rate of the polymer in presence of alkaline agents. Moreover the use of strongly alkaline agents (e.g. sodium or potassium hydroxide) limits the applicability of said technique to hydrolysis stable medicaments. In the EP-A1-0 204 476 the coating of nuclei of active agent with a film consisting of a biodegradable polymer and an agent promoting the formation of pores (e.g. saccharose) is disclosed. In this case the release is influenced by the porosity generated within the film by the dissolution of said agent. This involves however the use of different excipients in preparing the active agent-comprising cope and brings about factors which may influence, in a poorly controllable way, the preparing process, the chemical-physical stability and the release kinetic of the active agent. Moreover the coating of said nucleus adds one further technological stage to the manufacturing of the end product, which is a drawback from the view point of the production. In the EP-A$_2$-0092 918 and JP 2078 629 there is described the preparation of biodegradable block-copolymers constituted by a biodegradable hydrophobic part and an amphiphilic part capable of absorbing water and/or biological fluids to form a hydrogel able to control the release of the active agent. Such a technology involves the development of a new copolymer whose chemical nature is different from the "sum" of the chemical features of the starting products. Accordingly the biocompatibility properties of the end product are modified as well; it should moreover be considered that the usage of said product depends on the compliance with the protocols for the clearance of new products. In the EP-A$_2$-O 052 510 and U.S. Pat. No. 4,675,189 there is described a process for preparing particles which involves the presence of one or more agents modifying the polymer hydrolysis in order to modulate the release of the active agent. In this case too, the presence of said agents limits the possibility of application of said technique to hydrolysis stable medicaments. Finally the preparation of a polymer mixture by co-solubilizing homo- and copolymers belonging to the polyester class is disclosed in the EP-A$_1$- 0 281 482; such a mixture has a degradation rate higher than the single polymers. The application of said technique is however limited to the high molecular weight medicaments only, since the permeability of the polymer is not modified, thus the diffusion of low molecular weight medicaments is not modulated. Furthermore, because of the nature of the employed polymers (high molecular weight), such a technique limits itself with regard to the relative percentage of the employed polymers, consequently affecting the flexibility of the end system. The methods according to the aforementioned literature essentially try to modify the permeability or the degradation rate of the polymer in order to modulate the rate of release of the medicament. Said methods bring about different drawbacks, such as:

- addition of agents which may modify the molecular weight of the polymer, giving rise to the degradation of the same in noncontrollable way, already in the preparation phase of the microparticles;
- addition of several stages in the preparation process of the microparticles;
- synthesis of novel copolymers whose biocompatibility properties may dramatically change with respect to the starting homopolymers, since the chemical nature of the polymers is modified;
- addition of chemical agents which may affect the stability of the active agent within the microparticles of in any case which may limit the applicability of the technology.

SUMMARY OF THE INVENTION

Novel pharmaceutical compositions in the form of particles have now been found, which are able to overcome the drawbacks of the known prior art. Said pharmaceutical compositions comprise a biodegradable polymer and/of a polysaccharide jellifying and/of bioadhesive polymer, an amphiphilic polymer, an agent modifying the interface properties of the particles and a pharmacologically active substance. The preparation of such compositions comprises:

- the co-solubilisation of the polymeric constituents with the agent modifying the interface properties in presence of solvents, if any;

the solution or suspension of the active substance in the mixture of polymeric compounds;

the formation of particles consisting of the polymers, the agent modifying the interface properties and the active substance by techniques of emulsion of extrusion of spray-drying of spray-congealing. The thus obtained particles exhibit improved biocompatibility properties and allow a delayed release of the active substance.

DETAILED DESCRIPTION OF THE INVENTION

The features and advantages of the pharmaceutical compositions according to the present invention and the process fop preparing the same will be mope clearly evidenced by the following detailed description. As the first stage in preparing one of the formulations, a biodegradable polymer and/of a polysaccharide jellifying and/of bioadhesive polymer and an agent modifying the interface properties ape solubilized in an amphiphilic polymer. This manufacturing method proved to be particularly useful since it avoids the environmental problems and those problems concerning the potential toxicity of the solvents. As an alternative option, the polymers and the agent modifying the interface properties may be solubilized in the minimum necessary amount of solvent of solvent mixture. A pharmacologically active substance is then dissolved of dispersed in the polymer solution and the resulting solution of dispersion is emulsified by shaking in a suitable dispersing phase comprising agents able to modify the surface properties of the particles. In Order to avoid the diffusion of the amphiphilic polymeric component into the dispersing phase of the emulsion, said dispersing phase may comprise appropriate percentages of the same amphiphilic polymer. Moreover, in Order to decrease the likely partition of the active agent into the dispersing phase, the pH or the ionic strength of the same phase may be modified or still mixtures of solvents may be used. The dispersing phase of the emulsion may furthermore be saturated of the active agent. The shaking necessary to emulsify is carried out for time periods and at a speed suitable to obtain a completely emulsified product. The solvent, if present at all, is removed by evaporation. The particle suspension is centrifuged and/or filtered, optionally washed and the thus obtained product is dried in vacuum, by microwaves or lyophilized. The size of the thus obtained particles is in the range 0.1–150 μm. The equipment employed for emulsifying may be an emulsifier of the type rotor-stator capable of achieving the necessary rotation speed or any other type of emulsifier able to supply to the system the necessary energy for promoting the formation of the emulsion.

Another process, which may be used to prepare the particles constituted by the compositions object of the present invention, is based on the extrusion of the mass consisting of the biodegradable polymer or the jellifying/ bioadhesive polysaccharide, the amphiphilic polymer, the agent modifying the interface properties and the active agent. The extrusible mass may be obtained by dissolving the polymers and the agent modifying the interface properties in the amphiphilic polymer or in suitable amount of solvent. The materials may be either pre-mixed and fed into the preheated extrusor or heated, either alone or together before the extrusion or still heated by the heat generated during the extrusion itself. The optimum of temperature changes according to the employed polymers and to the amount of solvent, if present at all. The composition is extruded and then cooled. The extruded product may be obtained in the form of particles, beads or pellets, which are then micronized to the desired size. A still further process, which may be used for preparing the compositions in the form of the particles object of the present invention involves spray-drying the mixture consistiting of the polymers, the agent modifying the interface properties, the active agent and the solvent in a flow of warm air according to a classical method. As an alternative option, in the case of thermolabile active agents, the mixture may be sprayed in cold air flow (spray-congealing) to force the solvent comprised in the particles to congeal. The solvent may then be removed by lyophilisation. The particles according to the present invention may comprise a great deal of different active agents both synthetic and natural, comprising polypeptides. The following nonlimitative list shows same classes of pharmacologically active substances which may be used in the formulations of the present invention: central nervous system active medicaments, cardiovasculars, hypotensives, diuretics, antiphlogistics, analgesics, antipyretics, antiasthma, bronchodilatators, antitussives, mucolytics, antibiotics, chemotherapeutics, antivirus, hormones, antineoplastics, immunosupressors, immunostimulants, proteins, polypeptides, vaccines etc. Particularly preferred active substances are: nifedipine, diltiazem, diacereine, verapamil, captropril, magestrol acetate, temazepan, nicergoline, ibuprofen, piroxicam, naproxen, diclofenac, broxaterol and hydrochloride thereof, salbutamol, isoproterenol, albuterol, terbutaline, theophylline, beclometasone, desamethasone. Particularly preferred active substances of polypeptide type are: vasopressin, epidermic growth factor (EGF), luliberin or luteinizing hormon-release hormon (LH-RH), LH-RH analogues, (Des-Gly, D-Trp$^6$, Pro$^9$-ethylamide)-LH-RH analogue, somatostatin, somatotropin, interferon, calcitonin, encephalin, endorphin, angiotensin, heparin and derivatives, synthetic analogues and/or muteines or active fragments thereof. The solvents employed for preparing the compositions in the form of particles according to the invention are those classical for pharmaceutical use such as water, aqueous solutions with different pH-values, methanol, ethanol, methylene chloride, chloroform, acetonitrile, isopropylic alcohol, acetone, methylethylketone, etc. The biodegradable polymers comprise: polylactic acid, polyglycolic acid and co-polymers thereof, polyhydroxibutyric acid and copolymers thereof, polycaprolacton, polyorthoesters, polyanhydrides, chitins, chitosan, ialuronic acid, collagen and co-polymers thereof, etc. Suitable amphiphilic polymers comprise: polyethyleneglycols, polyvinylpyrrolidone, polyvinylalcohols, etc. Suitable jellifying and/or adhesive polysaccharide polymers comprise: scleroglucan, xanthan, chitins and chitosans, cellulose and derivatives, alginates, hylaluronic acid, etc. Agents able to modify the interface properties of the particles comprises: surface-active agents and mixtures thereof, for instance sorbitan esters, polysorbates, lecithins and other phospholipides, stearic acid, stearates and derivatives, etc. The percentage of the amphiphilic polymer relative to the biodegradable polymer and/or polysaccharide polymer may range from 0.1% to 99.9% and it is preferably comprised between 1% and 90% by weight. The percentage of the agents modifying the interface properties of the particles is comprised between 0.1% and 99.9% with regard to the polymers and preferably between 0.1% and 50% by weight. The percentage of the active substance in the compositions is comprised between 0.01% and 99.9% and preferably between 1% and 50% by weight. The features of the compositions of the invention may be evaluated according to different methods, such as:

determination of the permeability;

determination of the surface properties by estimating the contact angle solid/liquid;

scansion differential calorimetry to determine the thermic properties (glass transition temperature) and fusion temperature and enthalpy;

mercury porosimetry for determining the particle dimensional distribution. The compositions in the form of particles according to the invention show, when compared to those obtained according to known techniques, important advantages present either alone or simultaneously:

no hydrolysing agent is added, thus the polymer keeps its molecular weight;

no chemical agent is introduced, which may exert an influence on the stability of the active agent;

the chemical nature of the components is not modified;

the amphiphilic polymer may be used as solubilizer of the biodegradable polymer and/or polysaccharide polymer;

the amphiphilic polymer and the agent modifying the interface properties may be used as modulators of the solubility of the active agent.

Furthermore the obtained product exhibits the following desirable features:

the glass transition temperature of the biodegradable or polysaccharide polymer is decreased and therefore the permeability of the same polymer is modified (either decreased or increased) depending on the percentages and molecular weights of the amphiphilic polymers employed;

the modification of the permeability modulates both the release rate of the active substance and the degradation rate of the polymer;

at appropriate percentage of amphiphilic polymer there are two simultaneous phases with different thermic features;

the surface energy of the particles is decreased with resulting improved biocompatibility;

by using suitable ratios among biodegradable or polysaccharide polymers, amphiphilic polymer and agent modifying the interface properties, the best composition may be obtained with regard to the chemical-physical features of the active substance and having the desired release rate. The compositions in the form of particles of the present invention may be employed in manufacturing different pharmaceutical formulations among which the following are cited: injectable suspensions, inhalant suspensions or powders, rectal formulations, subcutaneous implants and oral formulations. Said compositions may in any case be suspended or mixed with suitable excipients which are normal in the pharmaceutical field. The following examples of preparation of compositions according to the present invention (examples 1 to 20) and comparative examples of formulations according to the known techniques (examples A-T) are hereinafter reported for illustrative, but not limitative purpose.

The characterization of the obtained products is discussed at the end of the examples.

EXAMPLE 1

1.5 gr co-poly (lactic-glycolic) acid (PLG 75:25) having i.v. (inherent viscosity) in $CHCl_3$ 0.74 dl/g (deciliters per gram) at 30° C. are dissolved in 30 ml methylene chloride with amounts of amphiphilic polymer (PEG 400) and agent modifying the interface properties (Tween 80°) corresponding to 10% and 0.5% relative to the PLG polymer. The solution is emulsified in 1200 ml distilled water comprising 0.1% Tween 80°. Shaking is maintained until complete evaporation of the solvent is achieved and the thus obtained particles are filtered, washed in distilled water and dried in vacuum. The size of the obtained product ranges from 1 and 10 μm.

EXAMPLE 2

The Example 1 is repeated with the difference that the used amount of Tween 80 is 1% relative to the PLG polymer.

EXAMPLE 3

The Example 1 is repeated with the difference that the used amount of Tween 80® is 1.5% relative to the PLG polymer.

EXAMPLE 4

The Example 1 is repeated with the difference that the used amount of PEG 400 is 2% relative to the PLG polymer.

EXAMPLE 5

The Example 1 is repeated with the difference that the used amount of PEG 400 is 5% relative to the PLG polymer.

EXAMPLE 6

The Example 1 is repeated with the difference that the used amount of PEG 400 is 20% relative to the PLG polymer.

EXAMPLE 7

The Example 1 is repeated with the difference that the used amount of PEG 400 is 30% relative to the PLG polymer.

EXAMPLE 8

The Example 1 is repeated with the difference that the used amount of PEG 400 is 40% relative to the PLG polymer.

EXAMPLE 9

The Example 1 is repeated with the difference that the used amount of PEG 400 is 50% relative to the PLG polymer.

EXAMPLE 10

1.5 gr co-poly (lactic-glycolic) acid (PLG 75/25, i.v. in $CHC_{13}$ 0.74 dl/g at 30° C.) are solved in 30 ml methylene chloride with amounts of polyethylene glycol 20.000 and lecithin corresponding respectively to 10% and 1% relative to the PLG polymer. Broxaterol base (150 mg) is dissolved in the solution and the mixture is emulsified in 1200 ml of 5% aqueous chitosan solution. Shaking is carried on until complete evaporation of the methylene chloride is achieved. The thus obtained particles comprising broxaterol base are centrifuged and dried in vacuum at temperature 40° C. The size of the obtained product ranges from 0.5 to 3 μm.

EXAMPLE 11

500 mg poly D,L-lactic acid (PLA) and 500 mg polyethylene glycol 4000 are dissolved in 20 ml methylene chloride with 0.1% sodium tauroxicholate and 20% magestrol acetate (percentage by weight on the total amount of polymers). The solution is emulsified in 800 ml 0.1% aqueous sodium tauroxicholate solution. Shaking is carried on until formation of the emulsion is achieved and the evaporation of the solvent is carried out in vacuum till complete elimination. Thus obtained particles ape centrifuged, filtered and dried in vacuum. The size of the product ranges from 40 to 125 μm.

EXAMPLE 12

600 mg co-poly (lactic-glycolic) acid (PLG 75/25) are dissolved in 12 ml methylene chloride/ethanol mixture 8/2 v/v with polyethylene glycol 2000 and 0.1% Tween 80 (percentage by weight on the amount of the PLG polymer). Nicergoline (240 mg) is dissolved in the solution and the mixture is emulsified in 400 ml 0.1% Tween 80 aqueous solution. Shaking is carried on until complete evaporation of the solvent is achieved and the thus obtained particles are centrifuged, filtered and dried in vacuum. The size of the obtained product ranges from 10 to 30 μm.

EXAMPLE 13

1.5 gram poly D,L-lactic acid (PLA) are dissolved in 30 ml methylene chloride comprising 3.5% polyethylene glycol 4000 and 1.5% Tween 60. 50 mg of ( Des-Gly-D-Trp$^6$, Pro$^9$-ethylene diamine)-LH-RH analogue solved in the lowest necessary amount of pure acetic acid are added to the solution. The solution is emulsified in 1200 ml distilled water comprising 3.5% polyethylenglycol 4000 and 1.5% Tween 60. Shaking is carried on until formation of the emulsion is achieved and the evaporation of the solvent is carried out in vacuum till complete elimination. Thus obtained particles are centrifuged and dried in vacuum. The size of the obtained product ranges from 20 to 45 μm.

EXAMPLE 14

200 mg co-poly (lactic-glycolic) acid (PLG 75/25) and 1 g stearic acid are dissolved in 24 ml methylene chloride comprising 18 mg polyethylene glycol 6000. Adriamycin (61 mg) is dissolved in the solution and the resulting solution is emulsified in 750 ml of 0.75% aqueous chitosan solution. Shaking is carried on until complete evaporation of the solvent is achieved and the thus obtained particles suspension is centrifuged and dried in microwave oven. The size of the obtained particles ranges from 10 to 40 μm.

EXAMPLE 15

50 gr co-poly (lactic-glycolic) acid (PLG 75/25, i.v. in CHCl$_3$ 0.52 dl/g at 30° C.) are solved in 2000 ml polyethylene glycol 200 comprising Tween 80® 2.5% relative to the PLG polymer. Salmon calcitonin (sCT) (1250 g) solved in the lowest necessary amount of pure acetic acid is added to the solution. Thus obtained solution is emulsified in 40 l of 2.5% Tween 80 solution in distilled water with pH adjusted to the sCT isoelectric point. Shaking is carried on until formation of the emulsion is achieved, the reactor is then brought in vacuum and the particles suspension is centrifuged in continuous through a 1 μm mesh rotating basket. Thus obtained particles have size ranging from 50 to 80 μm.

EXAMPLE 16

150 mg hyaluronic acid and 22.5 mg polyethyleneglycol 6000 are dissolved in 10 ml hexafluoroacetone hexahydrate comprising 5.2 mg stearic acid and 44.5 mg somatostatin. The solution is emulsified in 300 g liquid paraffin containing 0.1% sorbitan sesquioleate. Shaking is carried on until formation of the emulsion is achieved; thereafter vacuum is applied and the reactor temperature increased in order to promote the solvent evaporation. Thus obtained particles are centrifuged, filtered and washed with n-hexane to remove the residues of the emulsifying phase of the emulsion. The size ranges from 20 to 70 μm.

EXAMPLE 17

500 g polyethyleneglycol 6000 and 100 g co-poly(lactic-glycolic) acid (PLG 75/25) and 30 g stearic acid ape mixed with 630 mg broxaterol hydrochloride. The mixture is fed into a cochlea (Archimedean screw) extrusor, melted within the same extrusor and forced through a capillary drawplate. The melted product is recycled into the extrusor until the melted mass appears homogeneous in aspect and temperature. The drawn mass is then reduced to coarse beads with a rotating blade system and the thus obtained beads are then micronized with an air mill. The size of the obtained product ranges from 3 to 10 μm.

EXAMPLE 18

250 g co-poly (lactic-glycolic) acid (PLG 50/50), 250 g polyethyleneglycol 20.000 and 15 g lecithin are mixed with 77 g levonorgestrel. The mixture is fed into a cochlea (Archimedean screw) extrusor, melted within the same extrusor and forced through a capillary drawplate of suitable mesh. The melted product is recycled into the extrusor until the melted mass appears homogeneous in aspect and temperature. The drawn mass is then reduced to coarse beads with a rotating blade system and the thus obtained beads are then micronized with an air mill. The size of the obtained product ranges from 20 to 50 μm.

EXAMPLE 19

2.5 g polylactic acid (PLA) are dissolved in a methylene chloride/ethanol mixture 7/3 v/v with 3.5% polyethyleneglycol 4000 and 1.5% Tween 60 (percent by weight on the amount of the PLG polymer). LH-RH analogue (83.5 mg) is dissolved in the solution which is then dried by spray-drying. The size of the obtained particles ranges from 20 to 50 μm.

EXAMPLE 20

2 g of chitosan glutamate and 350 mg PEG 6000 are dissolved in a water/ethanol mixture 8/2 with 68 mg lecithin and 350 mg somatotropine. The solution is then sprayed into a chamber at temperature lower than the congealing temperature of the mixture water/ethanol. Thus obtained powder is lyophilized and the obtained particles have size ranging from 30 to 70 μm.

EXAMPLE A 1.5 gr co-poly (lactic-glycolic) acid (PLG 75/25, i.v. in CHCl$_3$ 0.74 dl/g at 30° C.) are solved in 30 ml methylene chloride. The solution is emulsified in 1200 ml distilled water comprising 0.1% of agent modifying the interface properties (Tween 80). Shaking is carried on until complete evaporation of the solvent is achieved and the thus obtained particles are filtered, washed with distilled water and dried in vacuum. The size of the obtained product ranges from 2 to 20 μm.

EXAMPLE B 1.5 gr co-poly (lactic-glycolic) acid (PLG 75/25, i.v. in $CHCl_3$ 0.74 dl/g at 30° C.) are solved in 30 ml methylene chloride with an amount of polyethyleneglycol (PEG 400) of 2% relative to the PLG. Said solution is emulsified in 1200 ml distilled water comprising 0.1% of Tween 80. Shaking is carried on until complete evaporation of the solvent is achieved and the thus obtained particles are filtered, washed with distilled water and dried in vacuum. The size of the obtained product ranges from 1 to 10 μm.

EXAMPLE C

The example B is repeated with the difference that the employed amount PEG 400 is 5% relative to the PLG.

EXAMPLE D

The example B is repeated with the difference that the employed amount PEG 400 is 10% relative to the PLG.

EXAMPLE E

The example B is repeated with the difference that the employed amount PEG 400 is 20% relative to the PLG.

EXAMPLE F

The example B is repeated with the difference that the employed amount PEG 400 is 30% relative to the PLG.

EXAMPLE G

The example B is repeated with the difference that the employed amount PEG 400 is 40% relative to the PLG.

EXAMPLE H

The example B is repeated with the difference that the employed amount PEG 400 is 50% relative to the PLG.

EXAMPLE I 1.5 gr co-poly (lactic-glycolic) acid (PLG 75/25, i.v. in $CHCl_3$ 0.74 dl/g at 30° C.) are solved in 30 ml methylene chloride with an amount of Tween 80 corresponding to the 0–5% relative to the polymer. Said solution is emulsified in 1200 ml distilled water comprising 0.1% of Tween 80. Shaking is carried on until complete evaporation of the solvent is achieved and the thus obtained particles are filtered, washed with distilled water and dried in vacuum. The size of the obtained product ranges from 1 to 10 μm.

EXAMPLE L

The example I is repeated with the difference that the employed amount Tween 80® is 1% relative to the polymer.

EXAMPLE M

The example I is repeated with the difference that the employed amount Tween 80® is 1.5% relative the polymer.

EXAMPLE N

The example I is repeated with the difference that the employed amount Tween 80® is 2.0% relative to the polymer.

EXAMPLE P 10 g polyethyleneglycol 20.000 and 50 mg Tween 80® are dissolved in 10 ml water/ethanol 50/50 v/v mixture. Said solution is dried by spray-drying and the size of the obtained particles ranges from 5 to 10 μm.

EXAMPLE Q 1.5 gr co-poly (lactic-glycolic) acid (PLG 75/25) are solved in 30 ml methylene chloride with 150 mg broxaterol base. Said solution is emulsified in 1200 ml distilled water comprising 0.1% of interface-active agent (Tween 80®). Shaking is carried on until complete evaporation of the solvent is achieved and the thus obtained microparticles are filtered, washed with distilled water and dried in vacuum. The size of the obtained product are comprised from 3 to 10 μm.

EXAMPLE R 600 mg co-poly (lactic-glycolic) acid (PLG 75/25) are solved in 12 ml methylene chloride/ethanol 8/2 v/v mixture with 240 mg nicergoline. Said solution is emulsified in 400 ml aqueous solution comprising 0.1% of interface-active agent (Tween 80®). Shaking is carried on until complete evaporation of the solvent is achieved and the thus obtained microparticles are filtered, washed with distilled water and dried in vacuum. The size of the obtained product are comprised from 10 to 50 μm.

EXAMPLE S 1 gr co-poly (lactic-glycolic) acid (PLG 75/25) is solved in 20 ml methylene chloride/ethanol 7/3 mixture with 50 mg adriamycin. Said solution is emulsified in 600 ml in 1% Tween 80 aqueous solution. Shaking is carried on until complete evaporation of the solvent and the thus obtained microsphere suspension is centrifuged and dried in microwave oven. The size of the obtained microspheres is comprised from 10 to 40 μm.

EXAMPLE T 1 gr co-poly (lactic-glycolic) acid (PLG 75/25) is solved in 20 ml methylene chloride. Salmon calcitonin (sCT) (25 mg) solved in the lowest necessary amount of pure acetic acid is added to the solution. Thus obtained solution is emulsified in 600 ml of 2.0% Tween 80 solution in distilled water with pH adjusted to the sCT isoelectric point. Shaking is carried on until formation of the emulsion is achieved, which is then brought in vacuum, keeping the shaking till complete evaporation of the solvent. Thus obtained microsphere suspension is centrifuged and dried in vacuum. The microspheres have size ranging from 30 to 50 μm.

CHARACTERIZATION TESTS

Hereinafter there are reported the description and results of the characterization tests of the compositions prepared according to the invention. Comparison tests with analogous compositions prepared according to known techniques are also reported.

SURFACE ENERGY FEATURES

A feature of the compositions prepared according to the present invention is the modification of the surface energy, which allows an improved biocompatibility to be obtained.

The modification of the surface energy is correlated to the wettability by the following equation:

$$\gamma_{sv} = \gamma_{sl} + \gamma_{lv} \cos(\theta)$$

where:
- $\gamma_{sv}$=surface energy solid/vapor
- $\gamma_{sl}$=surface energy solid/liquid
- $\gamma_{lv}$=surface energy liquid/vapor
- θ=contact angle liquid/solid.

For any material, $\gamma_{sv}$ may be split into a polar component and a dispersing component according to the equation:

$$\gamma_s(tot) = \gamma_s(p) + \gamma_s(d)$$

Said components may be calculated from experimental determinations of the contact angle and thereafter they may be included into the equation for the determination of the biocompatibility associated surface energy:

$$\gamma_{sl} = \gamma_s(tot) + \gamma_l(tot) - 4 \frac{\gamma_l(p)\gamma_s(p)}{\gamma_l(p)+\gamma_s(p)} - 4 \frac{\gamma_l(d)\gamma_s(d)}{\gamma_l(d)+\gamma_s(d)}$$

where: s=solid; l=liquid.

In the present case the values considered for the liquid are those relating to water, which is comparable to the physiological fluids which are in contact with the material in vivo. The modification of the surface energy, thus of the biodegradability, is correlated to the polarity of the material, which may be expressed in percents according to the equation:

$$\% P_l = \frac{\gamma_p \times 100}{\gamma_p + \gamma_d}$$

The method involves the determination of the contact angle (teta) between the surface of the material and a polar and/or non-polar liquid; said determination is carried out with a Lorentzen & Wetter apparatus equipped with a compartment for the evaporation of the same liquid. The data relating to some compositions comprising a biodegradable polymer and different percentages of amphiphilic polymer are reported by way of example in Table 1. In Table 2 and 3 there are reported data relating to the same biodegradable polymer in presence of an agent modifying the interface properties and the data relating to compositions comprising such a polymer, different percentages of amphiphilic polymer and the agent modifying the interface. As it can be appreciated, upon increase of the percent of the amphiphilic polymer, the surface energy of the interaction between solid and physiological liquid decreases (Tab. 1 col. 5) with consequent improved biocompatibility of the materials. Moreover the increase of the polarity (Tab. 1 col. 6) is a further indicator of the improved biocompatibility. From Table 2, column 5 and 6, the same trend as observed in the previous Table can be noted, though obtained with different percentages of the agent modifying the interface properties. From Table 3 it is evident the extent to which the association amphiphilic polymer/agent modifying the interface properties of the particle material object of the present invention brings about a synergism, which is derivable specifically from the data of surface energy and polarity (col. 5 and 6).

THERMIC PROPERTIES

In Table 4 there are reported the thermoanalytical data relative to the compositions in the form of particles prepared according to the invention as determinated using a scansion differential calorimeter Perkin-Elmer Mod. TAS 7. One of the feature of the products of the invention, is that either a composite homogeneous material or a material having phases with different features may be obtained upon modification of the percentage of the amphiphilic polymer. In the first case the decrease of the glass transition (Tg) temperature and accompanying variation in the permeability of the material, which increases or decreases depending on the percentages and molecular weights of the employed amphiphilic polymer, can be evidenced by thermic analysis (col. 3, percents from 2 to 20%). In the second case two clearly distinct transition events can be observed, one relative to the Tg of the polymeric component and one relative to the fusion temperature (Ft) of the amphiphilic polymer (col. 3 and 4, percents from 30% onwards). This is particularly useful in the case where the active substance is more compatible as regard to one of the polymeric materials. In column 5 there is reported the value of the melting enthalpy of the amphiphilic polymer. The increase in value of the delta H upon increase of the PEG percentage is an indicator of the amount of PEG responsible for the phenomenon of the phase separation. The adjustment of the permeability of the particles allows the controlled release of the active substance and thus the control of its activity to be attained.

ACTIVE SUBSTANCE RELEASE TESTS

The results of the tests concerning the release rate of the active substance from compositions according to the invention, when compared to compositions of the prior art are reported in Table 5 to 8.

TABLE 1

Data relative to some compositions comprising a biodegradable polymer and different percents of amphiphilic polymer.

| | Col. 1 % PEG | Col. 2 γ s | Col. 3 γ s | Col. 4 γ tot | Col. 5 γ sl | Col. 6 % P |
|---|---|---|---|---|---|---|
| ES.A | 0.0 | 12.39 | 30.57 | 42.96 | 24.62 | 28.84 |
| ES.B | 2.0 | 14.23 | 30.22 | 44.45 | 21.73 | 32.02 |
| ES.C | 5.0 | 15.27 | 29.08 | 44.35 | 19.98 | 34.44 |
| ES.D | 10.0 | 16.67 | 30.21 | 46.88 | 18.44 | 35.58 |
| ES.E | 20.0 | 20.03 | 30.94 | 50.97 | 14.78 | 39.38 |
| ES.F | 30.0 | 23.01 | 31.66 | 54.67 | 12.14 | 42.09 |
| ES.G | 40.0 | 25.35 | 31.57 | 56.91 | 10.12 | 44.53 |
| ES.H | 50.0 | 28.21 | 31.23 | 59.45 | 7.97 | 47.46 |
| ES.P | 100.0 | 39.48 | 32.27 | 71.76 | 3.30 | 55.01 |

PEG = percent amphiphilic polymer relative to the biodegradable polymer.
The "γ" are expressed in dyne/cm.

TABLE 2

Data relative to some compositions comprising a biodegradable polymer and an agent modifying the interface properties.

| | Col. 1 % T-80 | Col. 2 γ s | Col. 3 γ s | Col. 4 γ tot | Col. 5 γ sl | Col. 6 % P |
|---|---|---|---|---|---|---|
| ES.A | 0.0 | 12.39 | 30.57 | 42.96 | 24.62 | 28.84 |
| ES.I | 0.5 | 14.33 | 33.09 | 47.42 | 22.52 | 30.23 |
| ES.L | 5.0 | 15.27 | 29.08 | 44.35 | 19.98 | 34.44 |
| ES.M | 10.0 | 16.67 | 30.21 | 46.88 | 18.44 | 35.58 |
| ES.N | 20.0 | 20.03 | 30.94 | 50.97 | 14.78 | 39.38 |

The "γ" are expressed in dyne/cm.
% T-80 = percent of the agent modifying the interface properties relative to the polymer.

TABLE 3

Data relative to compositions comprising a biodegradable polymer and different percentages of amphiphilic polymer and agent modifying the interface properties.

| | Col. 1 % PEG % T-80 | Col. 2 γ s | Col. 3 γ s | Col. 4 γ tot | Col. 5 γ sl | Col. 6 % P |
|---|---|---|---|---|---|---|
| ES.A | 0.0 0.0 | 12.39 | 30.57 | 42.96 | 24.62 | 28.84 |
| ES.D | 10.0 0.0 | 16.67 | 30.21 | 46.88 | 18.44 | 35.58 |
| ES.I | 0.5 0.0 | 14.33 | 33.09 | 47.42 | 22.52 | 30.23 |
| ES.1 | 10.0 0.5 | 16.98 | 31.69 | 48.15 | 19.16 | 34.19 |
| ES.2 | 10.0 1.0 | 27.74 | 31.53 | 59.27 | 8.38 | 46.80 |
| ES.3 | 10.0 1.5 | 28.66 | 39.54 | 68.20 | 2.22 | 57.96 |

The % of PEG and T-80 are relative to the biodegradable polymer.

TABLE 4

Thermic properties of some products prepared according to the invention

| Col. 1 | Col. 2 % PEG | Col. 3 Tg(°C.) | Col. 4 Ft(°C.) | Col. 5 ΔH(J/g) | Notes |
|---|---|---|---|---|---|
| ES.1 | 0.0 | 25.24 | | | |
| ES.4 | 2.0 | 13.47 | | | |
| ES.5 | 5.0 | 10.06 | | | |
| ES.1 | 10.0 | 7.87 | | | |
| ES.6 | 20.0 | 6.03 | | | |
| ES.7 | 30.0 | 12.80 | 22.10 | 33.74 | separ. phase |
| ES.8 | 40.0 | 14.26 | 21.11 | 39.83 | separ. phase |
| ES.9 | 50.0 | 25.09 | 4.89 | 51.64 | separ. phase |
| ES.P | 100.0 | | 0.84 | 98.03 | |

% PEG relative to the PLG.
Ft is the fusion temperature of PEG
Each sample also comprises 0.5% T-80.

TABLE 5

Release rate from compositions comprising 10% broxaterol base.
RELEASE PERCENTAGE

| Time (hours) | 1 | 2 | 3 |
|---|---|---|---|
| 0.03 | 45.67 | | |
| 0.05 | 63.34 | | |
| 0.08 | 75.49 | 16.34 | 0.0 |
| 0.25 | 91.10 | 28.44 | 0.0 |
| 0.3 | 100 | | |
| 0.5 | | 42.71 | 9.89 |
| 1 | | 58.51 | 17.08 |
| 2 | | 84.55 | 23.18 |
| 4 | | 95.74 | 31.49 |
| 6 | | 100 | 37.39 |
| 24 | | 100 | 62.95 |

1 = Broxaterol base T.Q.
2 = Microspheres prepared according to the example 10.
3 = Microspheres prepared according to the example Q.

TABLE 6 release rate from compositions comprising 40% nicergoline
RELEASE PERCENTAGE

| Time (days) | 1 | 2 | 3 |
|---|---|---|---|
| 0.01 | 39.5 | | |
| 0.02 | 59.5 | 21.3 | 8.25 |
| 0.03 | 91.3 | | |
| 0.04 | 100 | 32.1 | 8.5 |
| 0.08 | 100 | 34.2 | 9.9 |
| 0.16 | | 37.1 | 12.5 |
| 1 | | 39.1 | 13.9 |
| 2 | | 42.5 | 15.7 |
| 3 | | 45.6 | 17.1 |
| 6 | | 49.3 | 23.8 |
| 8 | | 52.5 | 26.7 |
| 11 | | 58.2 | 30.2 |
| 15 | | 63.9 | 40.1 |
| 18 | | 69.3 | 44.2 |
| 24 | | 81.2 | 56.7 |
| 35 | | 100 | 71.4 |
| 42 | | | 80.9 |
| 48 | | | 89.2 |

1 = Nicergoline T.Q.
2 = Microspheres prepared according to the example 12.
3 = Microspheres prepared according to the example R.

TABLE 7

Release rate from compositions comprising 5% adriamycin.
RELEASE PERCENTAGE

| Time (hours) | 1 | 2 |
|---|---|---|
| 1 | 6.5 | 10.1 |
| 2 | 13.1 | 19.8 |
| 4 | 22.9 | 49.8 |
| 6 | 29.1 | 60.1 |
| 10 | 34.1 | 74.7 |
| 12 | 37.9 | 84.2 |
| 18 | 42.2 | 92.5 |
| 24 | 49.6 | 100 |
| 30 | 54.3 | |
| 40 | 65.4 | |
| 50 | 74.8 | |
| 60 | 84.6 | |
| 70 | 97.4 | |

1 = Microspheres prepared according to the example 14.
2 = Microspheres prepared according to the example S.

TABLE 8

Release rate from compositions comprising 2.5% salmon calcitonin.
RELEASE PERCENTAGE

| Time (days) | 1 | 2 |
|---|---|---|
| 1 | 15.1 | 3.5 |
| 2 | 28.6 | 8.3 |
| 3 | 38.1 | 15.1 |
| 4 | 42.1 | 20.5 |
| 5 | 47.3 | 23.8 |
| 8 | 67.8 | 35.2 |
| 10 | 75.3 | 40.8 |
| 13 | 87.5 | 49.6 |
| 15 | 99.6 | 58.3 |
| 20 | | 70.6 |

1 = Microspheres prepared according to the example 15.
2 = Microspheres prepared according to the example T.

We claim:

1. A pharmaceutical composition, in the form of particles having a diameter from 0.1 to 150 μm, suitable for the controlled release of a pharmaceutically active substance, comprising a biodegradable polymer, an amphiphilic polymer, an agent modifying the interface properties at a concentration between 0.1 and 99.9%, and a therapeutically effective amount of the pharmaceutically active substance at a concentration between 0.01 and 99.9% for those in need thereof, wherein said particles have separate intraparticle polymeric phases with different thermal characteristics when the content of the amphiphilic polymer is from 30 to 50% by weight relative to the biodegradable polymer.

2. The pharmaceutical composition according to claim 1, wherein said biodegradable polymer is selected from the group consisting of polylactic acid, polyglycolic acid and co-polymers thereof, polyhydroxybutyric acid, polycaprolacton, polyorthoesters, polyanhydrides, chitins, chitosans, hyaluronic acid, collagen and co-polymers thereof.

3. The pharmaceutical composition according to claim 1, wherein said amphiphilic polymer is selected from the group consisting of polyethyleneglycol, polyvinylpyrrolidone, and polyvinylalcohol.

4. The pharmaceutical composition according to claim 1, wherein said agents modifying the interface properties are agents selected from the group consisting of sorbitan esters, polysorbates, lecithins, stearic acid and stearates.

5. The pharmaceutical composition according to claim 1, wherein said pharmaceutically active substance is selected from the group consisting of central nervous system active medicaments, cardiovasculars, hypotensives, diuretics, antiphlogistics, analgesics, antipyretics, antiasthma, bronchodilatators, antitussives, mucolytics, antibiotics, chemotherapeutics, antivirus, hormones, antineoplastics, immunosuppressors, immunostimulants, proteins, polypeptides and vaccines.

6. The pharmaceutical composition according to claim 1, wherein said pharmaceutically active substance is calcitonin.

7. The pharmaceutical composition according to claim 1, wherein said pharmaceutically active substance is selected from the group of LH-RH analogues.

8. The pharmaceutical composition according to claim 1, wherein said pharmaceutically active substance is (Des-Gly, D-Trp$^6$, Pro$^9$-ethylamide) LH-RH analogue.

9. The pharmaceutical composition according to claim 1, wherein said pharmaceutically active substance is somatostatin.

10. The pharmaceutical composition according to claim 1, wherein said pharmaceutically active substance is somatotropin.

11. The pharmaceutically composition according to claim 1, wherein said pharmaceutically active substances are broxaterol and hydrochloride thereof.

12. The pharmaceutically composition according to claim 1, wherein said pharmaceutically active substance is nicergoline.

13. The pharmaceutical composition according to claim 1, wherein said pharmaceutically active substance is megesterol acetate.

14. The pharmaceutical composition according to claim 1, wherein said pharmaceutically active substance is adriamycin.

15. The pharmaceutical composition according to claim 1, wherein said pharmaceutically active substance is levonorgestrel.

16. The pharmaceutical composition according to claim 1, wherein the agent modifying the interface properties is present in an amount of between 0.1% and 50% by weight relative to the polymers.

17. The pharmaceutical composition according to claim 1, wherein the pharmaceutically active substance in the composition is present in an amount of between 1% and 50% by weight.

18. A pharmaceutical composition in the form of particles having a diameter from 0.1 to 150 μm, suitable for the controlled release of a pharmaceutically active substance, and having separate polymeric phases with different thermal characteristics, comprising a biodegradable polymer, an amphiphilic polymer present in an amount of from 30 to 50% by weight relative to said biodegradable polymer, an agent modifying the interface properties at a concentration between 0.1% and 99.9%, and a therapeutically effective amount of said pharmaceutically active substance at a concentration between 0.01% and 99.9% for those in need thereof.

19. The pharmaceutical composition according to claim 18, wherein said biodegradable polymer is selected from the group consisting of polylactic acid, polyglycolic acid and co-polymers thereof, polyhydroxybutyric acid, polycaprolacton polyorthoesters, polyanhydrides, chitins, chitosans, hyaluronic acid, collagen and co-polymers thereof.

20. The pharmaceutical composition according to claim 18, wherein said amphiphilic polymer is selected from the group consisting of polyethyleneglycol, polyvinylpyrrolidone and polyvinylalcohol.

21. The pharmaceutical composition according to claim 18, wherein said agents modifying the interface properties are agents selected from the group consisting of sorbitan esters, polysorbates, lecithins, stearic acid and stearates.

22. The pharmaceutical composition according to claim 18, wherein said pharmaceutically active substance is selected from the group consisting of central nervous system active medicaments, cardiovasculars, hypotensives, diuretics, antiphlogistics, analgesics, antipyretics, antiasthma, bronchodilatators, antitussives, mucolytics, antibiotics, chemotherapeutics, antivirus, hormones, antineoplastics, immunosuppressors, immunostimulants, proteins, polypeptides and vaccines.

23. The pharmaceutical composition according to claim 18, wherein said pharmaceutically active substance is calcitonin.

24. The pharmaceutical composition according to claim 18, wherein said pharmaceutically active substance is selected from the group of LH-RH analogues.

25. The pharmaceutical composition according to claim 18, wherein said pharmaceutically active substance is (Des-Gly, D-Trp$^6$, Pro$^9$-ethylamide) LH-RH analogue.

26. The pharmaceutical composition according to claim 18, wherein said pharmaceutically active substance is somatostatin.

27. The pharmaceutical composition according to claim 18, wherein said pharmaceutically active substance is somatotropin.

28. The pharmaceutical composition according to claim 18, wherein said pharmaceutically active substances are broxaterol and hydrochloride thereof.

29. The pharmaceutical composition according to claim 18, wherein said pharmaceutically active substance is nicergoline.

30. The pharmaceutical composition according to claim 18, wherein said pharmaceutically active substance is megesterol acetate.

31. The pharmaceutical composition according to claim 18, wherein said pharmaceutically active substance is adriamycin.

32. The pharmaceutical composition according to claim 18, wherein said pharmaceutically active substance is levonorgestrel.

33. The pharmaceutical composition according to claim 18, wherein the agent modifying the interface properties is present in an amount of between 0.1% and 50% by weight relative to the polymers.

34. The pharmaceutical composition according to claim 18, wherein the pharmaceutically active substance in the composition is present in an amount of between 1% and 50% by weight.

* * * * *